US00PP30614P2

(12) United States Plant Patent
van der Voort

(10) Patent No.: US PP30,614 P2
(45) Date of Patent: Jun. 25, 2019

(54) ***AGASTACHE* PLANT NAMED 'AGAPD'**

(50) Latin Name: ***Agastache* hybrid**
Varietal Denomination: Agapd

(71) Applicant: Van Hemert & Co. BV, Hazerswoude (NL)

(72) Inventor: Rob van der Voort, Hazerswoude (NL)

(73) Assignee: VAN HEMERT & CO. BV, Hazerswoude (NL)

( * ) Notice: Subject to any disclaimer, the term of this patent is extended or adjusted under 35 U.S.C. 154(b) by 0 days.

(21) Appl. No.: 15/932,627

(22) Filed: Mar. 28, 2018

(51) Int. Cl.
*A01H 5/02* (2018.01)

(52) U.S. Cl.
USPC ..... Plt./399

(58) Field of Classification Search
USPC ..... Plt./263.1, 399
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Agastache* named 'Agapd' that is characterized by its good performance in humid climates, its numerous flowers that are purple in color, its foliage that is dark green in color, its compact and well branched plant habit, its good winter hardiness, and its ability to be readily and quickly produced by cuttings.

2 Drawing Sheets

Botanical classification: *Agastache* hybrid.
Variety denomination: 'Agapd'.

BACKGROUND OF THE INVENTION

The present invention relates to a new and distinct cultivar of *Agastache* hybrid and will be referred to hereafter by its cultivar name, 'Agapd'. 'Agapd' is an herbaceous perennial grown for landscape use.

'Agapd' arose as part of an ongoing breeding program conducted by the Inventor in Hazerswoude, The Netherlands with the goal of developing new cultivars of *Agastache* with well-branched and compact plant habits, healthy foliage, resistance against fungal diseases, long flower spikes and unique flower colors.

'Agapd' derived from open pollination of an unnamed and unpatented proprietary plant of *Agastache* from the Inventor's breeding program in August of 2009. The male parent is therefore unknown. The new cultivar was selected from amongst the resulting seedlings as a single unique plant in July of 2010.

Asexual propagation of the new cultivar was first accomplished by the Inventor by stem cuttings in May of 2011 in Hazerswoude, The Netherlands. Asexual propagation of the new cultivar by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Agapd' as a unique cultivar of *Agastache*.

1. 'Agapd' exhibits good performance in humid climates (typically a problem with many *Agastache* cultivars).
2. 'Agapd' exhibits numerous flowers that are purple in color.

3. 'Agapd' exhibits foliage that is dark green in color.
4. 'Agapd' exhibits a compact and well branched plant habit.
5. 'Agapd' exhibits good winter hardiness.
6. 'Agapd' exhibits the ability to be readily and quickly produced by cuttings.

The female parent of 'Agapd', is similar to 'Agapd' in flower color. The female parent of 'Agapd' differs from 'Agapd' in having flowers that are less intense purple in color and flower spikes that are shorter in length. 'Agapd' can be compared to the cultivar *Agastache rugosa* 'Little Adder' (U.S. Plant Pat. No. 26,514). 'Little Adder' is similar to 'Agapd' in having a compact plant habit. 'Little Adder' differs from 'Agapd' in having flowers with a less intense purple color and flower spikes that are thinner.

BRIEF DESCRIPTION OF THE DRAWINGS

The accompanying colored photographs illustrate the overall appearance and distinct characteristics of a 4-month-old plant of the new *Agastache* as grown in a 25-cm container in Hazerswoude, The Netherlands.

The photograph in FIG. 1 provides a side view of 'Agapd' in bloom.

Figure 1:
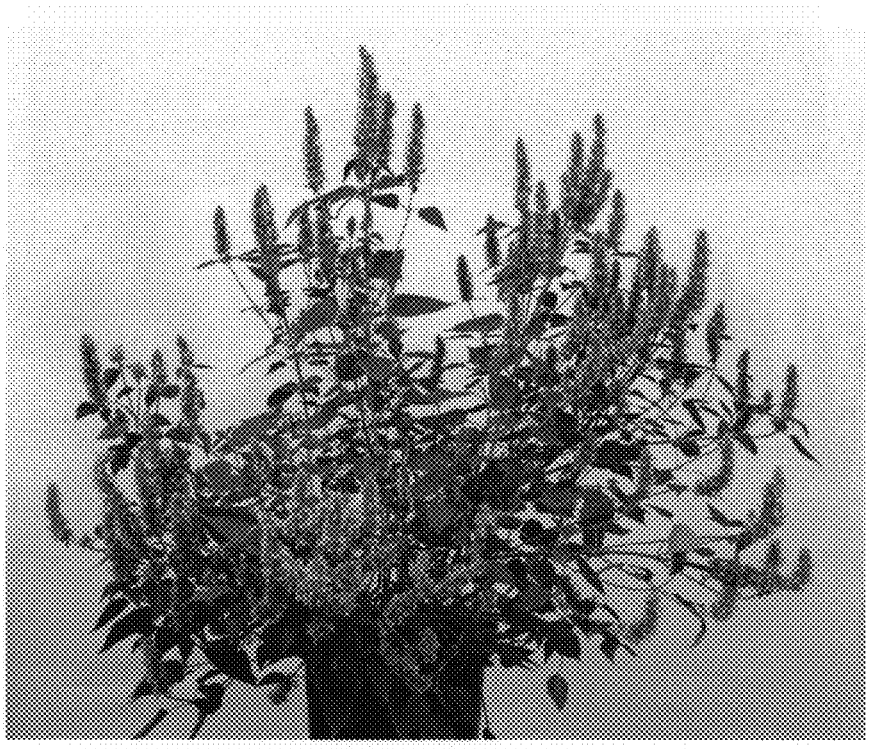
Figure 2:
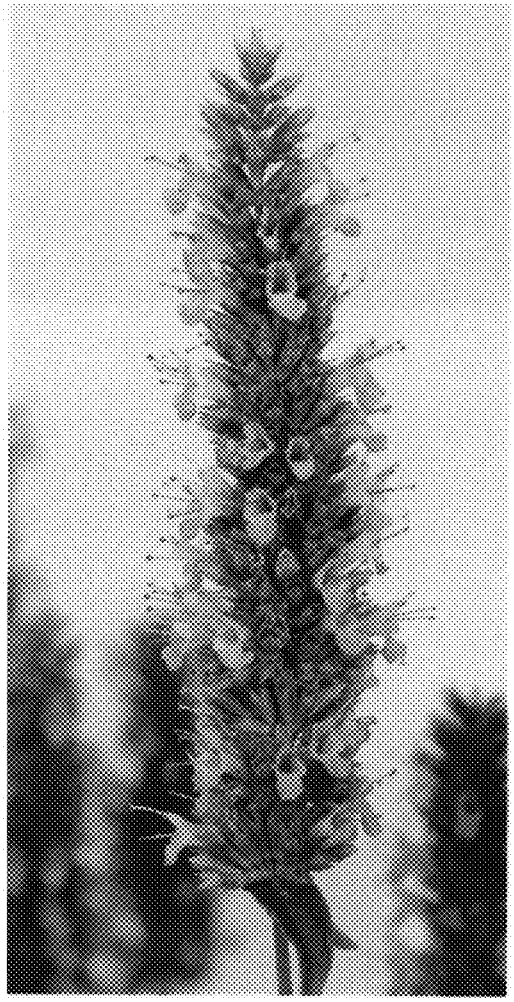

The photograph in FIG. 2 provides a close-up view of an inflorescence of 'Agapd'.

The colors in the photographs may differ slightly from the color values cited in the detailed botanical description, which accurately describe the colors of the new *Agastache*.

DETAILED BOTANICAL DESCRIPTION

The following is a detailed description of the new cultivar of plants 4 months in age as grown outdoors in 25-cm containers in Hazerswoude, The Netherlands. The plants were grown under average day temperatures of 15° C. to 30° C. and average night temperatures of 6° C. to 18° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Later spring into summer in The Netherlands.

*Plant type*.—Herbaceous perennial.

*Plant habit*.—Upright, broad spreading.

*Plant size*.—Average of 30 cm in height and 45 cm in width.

*Cold hardiness*.—At least in U.S.D.A. Zones 7 to 11.

*Diseases and pests*.—No susceptibility or resistance to diseases or pests has been observed.

*Root description*.—Fibrous and fine.

*Root development*.—About 4 to 5 weeks to initiate roots and 6 to 8 weeks to fully root as a young plant.

*Propagation*.—Stem cuttings.

*Growth rate*.—Moderate to high.

Stem description:

*Shape*.—Quadrangular.

*Stem color*.—Young stem; 143C, mature stems; 143A, fading towards the base to 197A.

*Stem size*.—Average of 51 cm in length, 4 mm in diameter.

*Stem surface*.—Slightly glossy and densely covered with very short glandular hairs, average of 0.1 mm in length and too small to measure color.

*Stem aspect*.—Held at varying angles between 20° to 90°, secondary lateral branches in an average angle of 30° to primary branches.

*Internode length*.—Average of 2.7 cm.

*Branching*.—Average of 21 primary branches and 6 lateral branches.

*Stem strength*.—Moderately strong.

Foliage description:

*Leaf shape*.—Ovate to near deltoid.

*Leaf division*.—Simple.

*Leaf base*.—Truncate.

*Leaf apex*.—Apiculate.

*Leaf venation*.—Pinnate, upper surface color; 147C, lower surface color; 147D.

*Leaf margins*.—Serrate.

*Leaf arrangement*.—Opposite.

*Leaf attachment*.—Petiolate.

*Leaf surface*.—Both surfaces are smooth, slightly rugose, matte, densely pubescent with very short glandular hairs; an average of 0.1 mm in length and too small to measure color.

*Leaf size*.—Average of 7.6 cm in length and 5.2 cm in width.

*Leaf color*.—Young upper surface; 137A, young lower surface; 138A, mature upper surface; NN137A, mature lower surface; 147A.

*Fragrance*.—Sweet minty fragrance when touched.

*Petioles*.—An average of 4 cm in length and 1.5 mm in diameter, upper and lower surface color between 138B and 143C, moderately strong, both surfaces are smooth and densely covered with short glandular hairs an average of 0.1 mm in length and too small to measure color.

Inflorescence description:

*Inflorescence type*.—Terminal raceme of labiate flowers.

*Lastingness of inflorescence*.—Individual flowers average of 10 days, self cleaning.

*Inflorescence size*.—An average of 11.6 cm in height and 3.1 cm in diameter.

*Flower type*.—Labiate.

*Flower aspect*.—Outward, freely flowering.

*Flower number*.—Average of 300 per inflorescence.

*Flower fragrance*.—None.

*Flower buds*.—Obovate in shape, 6 mm in length, 2.5 mm in diameter, matte surface, immature petals and free calyx tips color 76C, immature calyx tube color 144D.

*Flower size*.—Average of 5.5 mm in height, 3 mm in diameter, 1.6 cm in length, throat diameter is 2 mm, tube length is 9 mm, tube diameter 2.5 mm.

*Peduncle*.—An average of 10.2 cm in length and 1.25 mm in diameter, 144B to 144C in color, held straight on top of lateral branch, moderately strong in strength, surface is matte and moderately pubescent with glandular hairs an average of 0.1 mm in length and too small to measure color.

*Pedicels*.—Average of 2 mm in length, 0.5 mm in diameter, 144A in color, held at an average angle of 45° (0°=straight upright), moderately weak in strength.

*Calyx*.—Rotate and tubular in shape, average of 7 mm in length and 2 mm in diameter.

*Sepals*.—5, rotate, 1 whorl, base is fused 27.5%, obovate in shape, entire margin, acute apex, 7 mm in length, 1 mm in width, entire margins, upper and lower surface smooth, glabrous and matte, when opening upper and lower surface 144D, free apex 76C, fully open upper and lower surface 144D, free apex tinged 76C.

*Petals*.—5 (4 similar petals and 1 odd-shaped lower petal), 1 whorl, fused at base 80%, labiate, upper lip; oblanceolate in shape, margin entire, apex obtuse, 1.1 cm in length and 1.5 mm in width, based fused, upper and lower surface smooth, matte, glabrous, color when opening upper and lower surface 76C, fully open upper and lower surface 85C, fading upper and lower surface N88B to N88C, throat 85C, tube 85D fading to NN155D at the base, lower lip; oblanceolate in shape, margin entire, apex of lower cleft into two lobes, tip of lobes praemorse, 1.2 cm in length and 3 mm in width, base fused, upper and lower surface smooth, matte, glabrous, color when opening upper and lower surface 76C, fully open upper and lower surface 85B, fading upper and lower surface N88B to N88C, throat 85C, tube 85D fading to NN155D at the base.

Reproductive organs:

*Gynoecium*.—Pistil; 1, 8 mm in length, style; 7.5 mm in length, 91D in color, stigma; cleft (2 parted), 0.3 mm in diameter and 91C in color, ovary; N144A to 144B in color.

*Androcoecium*.—Stamens; 4, filaments; 4, implanted in flower tube, up to 7 mm in length, 91A, fading lighter towards the base to 91B in color, anthers; dorsifixed, narrow elliptic in shape, 0.5 mm in length and width, N92A in color, pollen; moderate in quantity and 8A in color.

*Fruit and seed*.—None have been observed to date.

It is claimed:

1. A new and distinct cultivar of *Agastache* plant named 'Agapd' as herein illustrated and described.

* * * * *